United States Patent
Maki, Jr.

[11] Patent Number: 6,151,963
[45] Date of Patent: Nov. 28, 2000

[54] APPARATUS AND METHOD FOR EVALUATING THE EFFECTIVENESS OF MATERIALS REMOVAL BY A FLUID

[75] Inventor: Voldi E. Maki, Jr., Austin, Tex.

[73] Assignee: Dresser Industries, Houston, Tex.

[21] Appl. No.: 09/138,725

[22] Filed: Aug. 24, 1998

[51] Int. Cl.[7] .................................................. G01F 23/00
[52] U.S. Cl. ...................................................... 73/304 R
[58] Field of Search ............................... 73/61.43, 61.44, 73/64.48, 152.28, 152.34, 290 R, 304 R, 304 C

[56] References Cited

U.S. PATENT DOCUMENTS

| | | |
|---|---|---|
| 3,286,510 | 11/1966 | Parker . |
| 4,253,064 | 2/1981 | McBride, Jr. ............................ 324/436 |
| 4,259,868 | 4/1981 | Rao et al. . |
| 4,380,266 | 4/1983 | Wellington . |
| 4,409,662 | 10/1983 | Rao . |
| 4,430,889 | 2/1984 | Sutton . |
| 4,567,765 | 2/1986 | Rao et al. . |
| 4,648,264 | 3/1987 | Freese et al. . |
| 4,691,558 | 9/1987 | Vinson et al. . |
| 4,700,567 | 10/1987 | Frey et al. . |
| 4,823,594 | 4/1989 | Gray . |
| 4,873,648 | 10/1989 | Mouser et al. . |
| 4,888,098 | 12/1989 | Nyberg et al. ........................... 205/766 |
| 5,097,248 | 3/1992 | Kumada et al. ........................... 338/80 |
| 5,237,857 | 8/1993 | Dobson et al. ......................... 73/61.44 |
| 5,325,723 | 7/1994 | Meadows et al. . |
| 5,329,811 | 7/1994 | Schultz et al. . |
| 5,542,289 | 8/1996 | Hool et al. .............................. 73/64.52 |

*Primary Examiner*—Max Noori
*Attorney, Agent, or Firm*—Browning Bushman

[57] ABSTRACT

An apparatus and method for wettability measurements are provided. The apparatus includes a surface having a pair of electrodes separated by an insulator affixed thereto. The electrodes are operable for supporting an oil film, and the may be immersed in a surfactant solution. Circuitry for measuring the complex impedance between the electrodes is coupled to the electrodes. The capacitive part of the complex impedance provides a measure of the oil thickness as it is removed by the surfactant solution. A rotating member is provided for agitating the surfactant solution thereby modifying the effectiveness of the solution in removing the film.

34 Claims, 4 Drawing Sheets

Block Diagram

APPARATUS AND METHOD FOR EVALUATING THE EFFECTIVENESS OF MATERIALS REMOVAL BY A FLUID

TECHNICAL FIELD

The present invention relates in general to oil well drilling, and in particular, to the measurement of the effectiveness of chemicals to remove the oil film resulting from oil-based drilling mud.

BACKGROUND INFORMATION

In the process of drilling an oil well, it is sometimes necessary to use a drilling mud based on oil rather than water. This oil-based mud wets the well casing and the formation surrounding the well. If the resulting oil film is not removed, the cement which is used to seal the casing to the formation will not adhere to either the casing or the formation.

Chemicals may be pumped into the well to effect removal of the oil film. The chemicals include surfactants in a salt solution. The efficacy of these fluids in removing the oil film may depend on the composition as well as mechanical agitation of the solution. The effectiveness of film removal may be increased by the shearing force resulting from the motion of the clean-up fluid.

The time needed to remove the oil film may depend both on the surfactant formulation and the shear rates generated in the solution. Surfactant solutions must be tested to determine their effectiveness in removing the oil film. Additionally, the efficacy of agitation generated shear forces must also be tested and the application time needed to remove the film determined. Downhole tests require an expensive wireline tool to be implemented at the well. Moreover, currently, no tool exists for making the desired measurements. Together, these make the cost of downhole measurements prohibitive.

Thus, there is a need in the art for an economical apparatus and method for the measurement of the effectiveness of these chemicals in removing an oil film in the presence of shear flows.

SUMMARY OF THE INVENTION

The aforementioned needs are addressed by the present invention. Accordingly there is provided, in a first form, an apparatus for wettability measurement including an annular member having an inner surface, the annular member being adaptable for immersion in a fluid, and first and second electrodes affixed to the inner surface of the annular member, wherein the electrodes each have a surface operable for supporting an oil film. An insulator is affixed to the inner surface and disposed between the first and second electrodes, the first and second electrodes being adapted for measuring a complex impedance therebetween. The complex impedance provides a measure of wettability. The apparatus also includes a rotatable member operable for generating shear forces in the fluid, the shear forces for modifying an oil film producing a water wet surface.

There is also provided, in a second form, a method of wettability measurement including the step of immersing a pair of electrodes operable for supporting an oil film in a conducting solution. The method further includes determining a complex impedance between the electrodes.

It will be understood that as is sometimes used herein, expressions relating to the measurement of "wettability" are used to identify a process for evaluating a material that affects the wettability of another material.

The foregoing has outlined rather broadly the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1A:
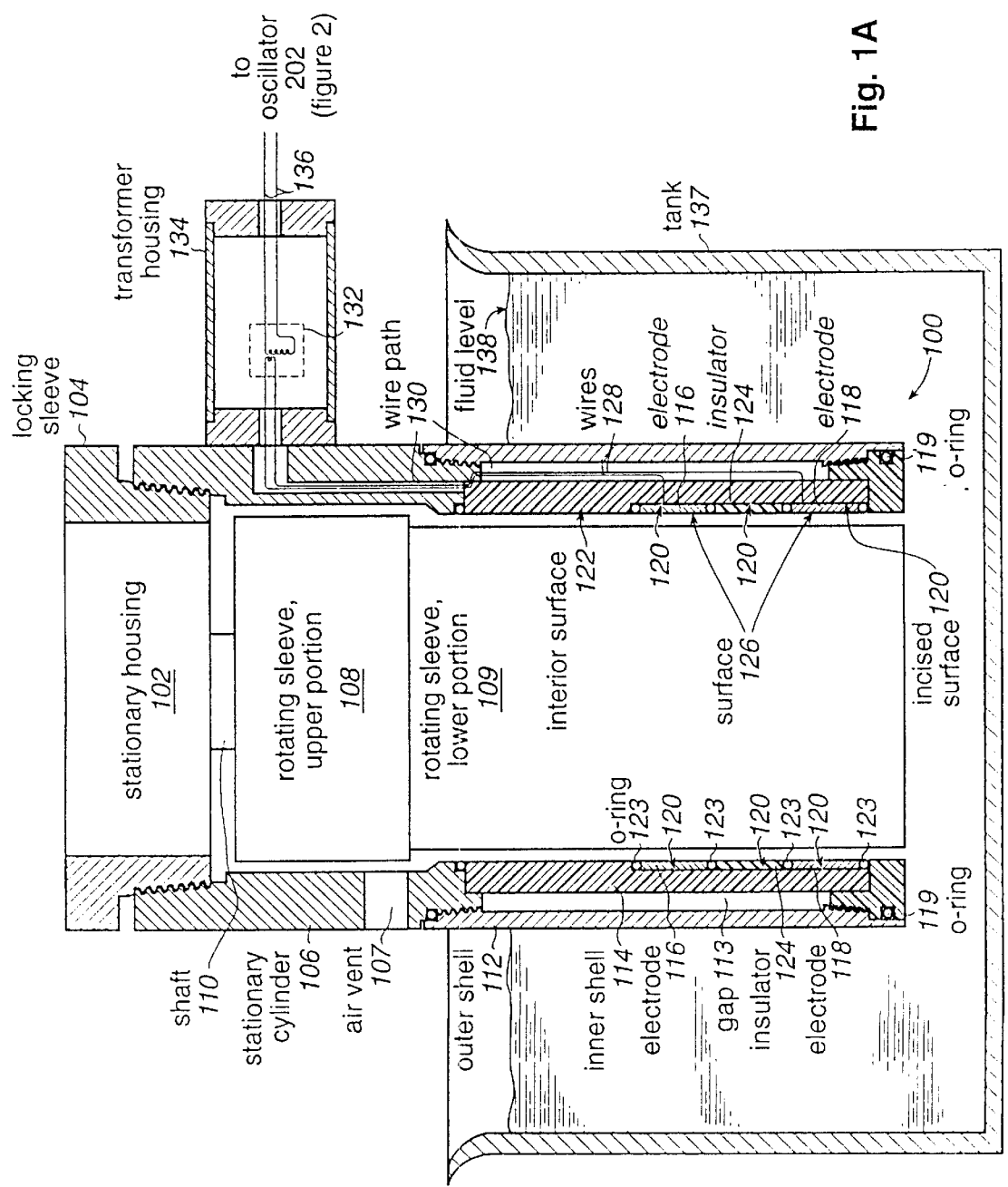
FIG. 1A illustrates, in cross-sectional elevation view, a wettability cell according to an embodiment of the present invention.

The present invention provides an apparatus for the effectiveness of measurement of the oil film removal by an aqueous solution of surfactants in the presence of a shear flow. The surfactants promote the dissolution of the oil film and thereby promote wetting of the surfaces by water. Dissolution of the oil film may be further enhanced by agitation producing shear forces in the solution. A pair of oil film coated electrodes is immersed in the surfactant solution. A shear flow is generated by a rotating cylinder. An alternating current signal is passed between the electrodes, and the complex impedance presented to the electrodes by the oil film and surfactant solution system is measured. A capacitive portion of the complex impedance provides a measure of the thickness of the oil film. The complex impedance has a conductive portion due to the inclusion of salt in the surfactant solution. In an offshore drilling environment, salt is naturally occurring in seawater used to make up the solution. In an on-shore well, the surfactants may be added to salt water recovered from the well; a saline surfactant solution protects the formation.

In the following description, numerous specific details are set forth such as specific capacitances and rotation speeds, etc. to provide a thorough understanding of the present invention. However, it will be obvious to those skilled in the art that the present invention may be practiced without such specific details. In other instances, well-known circuits have been shown in block diagram form in order not to obscure the present invention in unnecessary detail.

Refer now to the drawings wherein depicted elements are not necessarily shown to scale and wherein like or similar elements are designated by the same reference numeral through the several views.

Referring to FIG. 1, there is illustrated, in cross-sectional view, wettability cell 100 for measuring the effectiveness of oil film removal according to the present invention. Cell 100 includes stationary housing 102 fitted with threaded locking sleeve 104. Stationary cylinder 106 is threaded onto locking sleeve 104 and envelopes rotating sleeve upper portion 108 which is coupled by shaft 110 to a drive means (not shown) within stationary housing 102, and rotating sleeve lower portion 109 which is friction fit into upper portion 108. The drive means may, in an embodiment of the present invention, be a conventional drive means, such as an electric motor. Stationary cylinder 106 also has air vent 107 passing therethrough. An embodiment of stationary housing 102, locking sleeve 104, upper portion 108, lower portion 109, and shaft 110 may constitute a portion of a commercial viscometric cell, such as a Fann 35A, manufactured by Fann Instruments Company.

A lower portion of stationary cylinder 106 includes metallic outer shell 112 and insulating inner shell 114. Gap 113 separates outer and inner shells 112 and 114. Gap 113 is sealed at its lower end by seal 117 and o-ring 119. A pair of conducting electrodes, electrode 116 and electrode 118 are affixed against an incised surface 120 of interior surface 122 of inner shell 114 and disposed about a circumference thereof. In an embodiment of the present invention, electrodes 116 and 118 may be steel. Electrode 116 and electrode 118 are separated by insulator 124 that is also affixed against incised surface 120 and disposed about a circumference of incised surface 120.

Figure 1B:
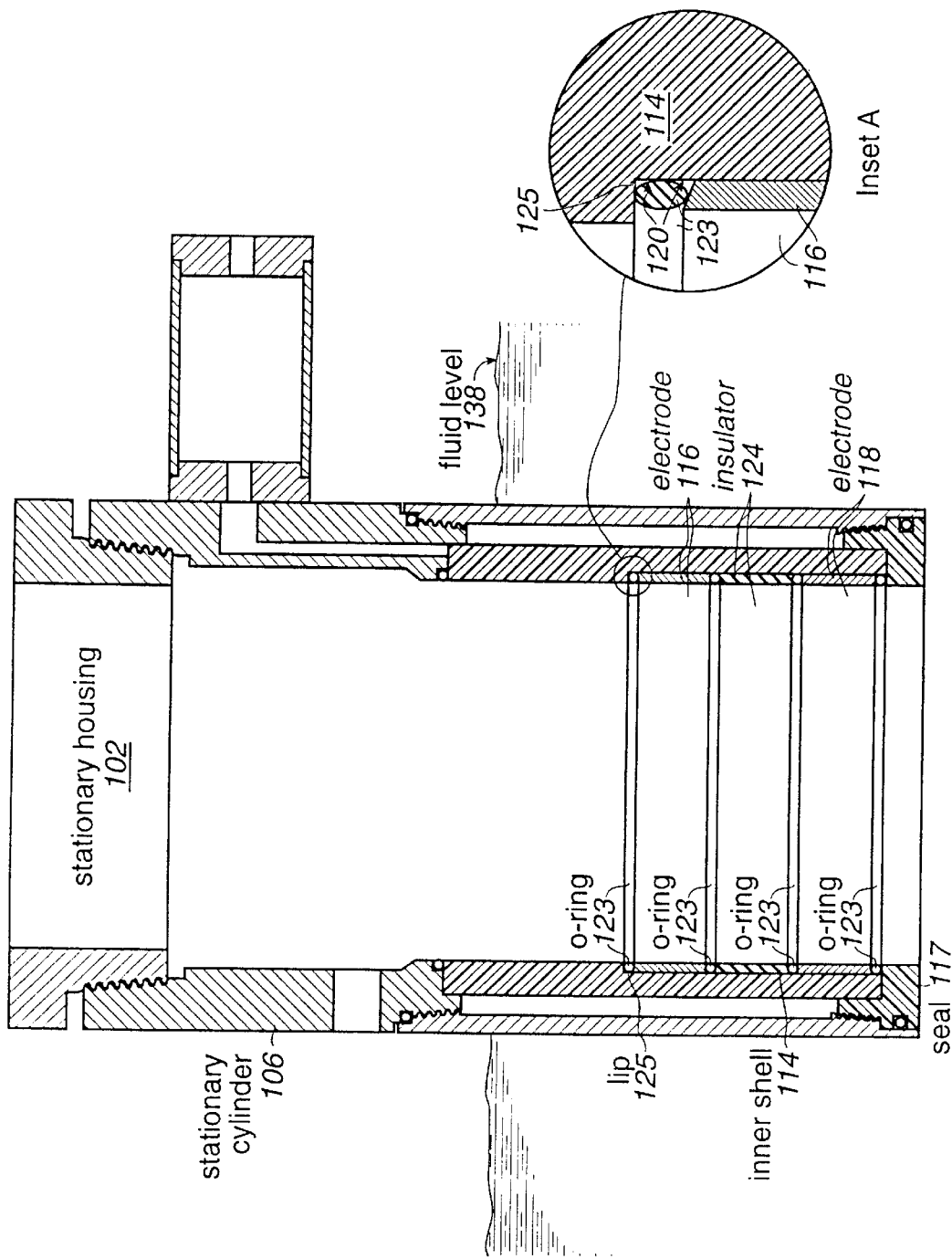
FIG. 1B illustrates, in cross-sectional elevation view a wettability cell according to an embodiment of the present invention having a portion removed to reveal obscured structure.

The structure of electrodes 116 and 118, insulator 124 and o-rings 123 may be further understood by referring to FIG. 1B illustrating cell 100 with rotating sleeve portions 108 and 109 removed. Certain reference numerals have been omitted from FIG. 1B for clarity. O-rings 123 span the circumference of incised surface 120 and separate electrodes 116 and 118 from insulator 124, separate electrode 118 and seal 117, and separate electrode 116 and lip 125 of inner shell 114. Electrodes 116 and 118, o-rings 123 and insulator 124 are retained in shell 114 by seal 117.

Inset "A" illustrates lip 125 and incised surface 120 in greater detail. O-ring 123 is confined vertically between lip 125 and electrode 116, and forms a seal therebetween. O-ring 123 and electrode 116 horizontally abut incised surface 120 of inner shell 114.

Returning to FIG. 1A, surfaces 126 of electrode 116 and 118 support the oil film to be removed during the operation of cell 100. Electrodes 116 and 118 are coupled, by a respective one of a pair of wires 128, to electronic circuitry external to cell 100 for measuring a complex impedance. (Such circuitry will be discussed in conjunction with FIG. 2.) Wires 128 pass through gap 113 and then through wire path 130 in stationary cylinder 106 and connect to a primary of transformer 132 which is contained in transformer housing 134 attached to stationary cylinder 106. Transformer 132 is a step-up device thereby raising the complex impedance presented by wettability cell 100 to the external circuitry. A pair of wires 136 connects a secondary of transformer 132 to the external circuitry, including oscillator 202, in FIG. 2.

In operation, oil is introduced onto electrodes 116 and 118 by immersing cell 100 into an oil-based mud to a depth sufficient to cover the electrodes and rotation of sleeve portions 108 and 109 coats surfaces 126 with the oil and suspended particulates. (Oil-based mud constitutes an oil with suspended particulates to increase the density of the oil.). The mud film initially may have a thickness of approximately 25–30 thousandths of an inch (0.025"–0.030"). Cell 100 is then immersed in tank 137 containing the surfactant solution under test to a predetermined fluid level 138. Salt is included in the solution making it conductive. In the drilling environment, salt occurs naturally, as discussed above. Shear forces are produced in the surfactant solution by rotation of rotating sleeve portions 108 and 109. This simulates the shear force in the fluid due to the flow of the surfactant solution in the well bore environment wherein the solution flows from an end of the drill pipe and up the casing. The fluid may also be used as a spacer fluid in which case it is pumped down the casing and then up a gap between the casing and formation. The vertical flow in the gap generates a shear force between the fluid and the casing and formation. Electrodes 116 and 118, bearing the oil film to be removed on surfaces 126, are coupled to the external circuitry for measuring the complex impedance between electrodes 116 and 118.

Figure 2:
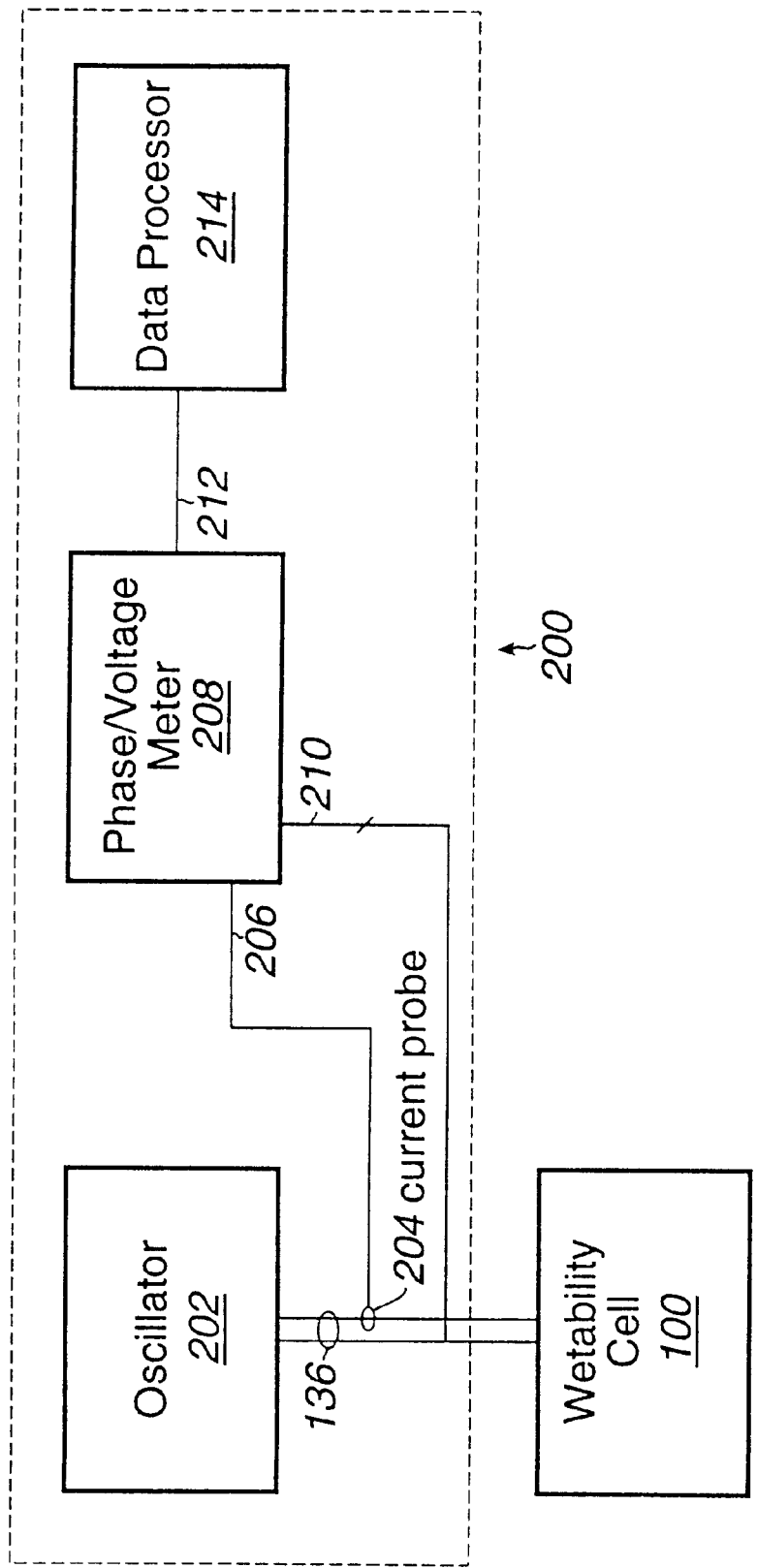
FIG. 2 illustrates, in block diagram form, circuitry for measuring a complex impedance in a wettability cell in accordance with an embodiment of the present invention.

Refer now to FIG. 2 illustrating a block diagram of circuit 200 for measuring the complex impedance between electrodes 116 and 118. Oscillator 202 provides an alternating current (AC) signal via wires 136 to wettability cell 100. Oscillator 202 may be embodied in a commercial signal generator unit such as a Hameg 8130 signal generator, manufactured by Hameg, Inc. The frequency of the AC signal output from generator 202 may, preferably, be in a range from 10 kHz to 1 MHZ. The current delivered by oscillator 202 to wettability cell 100 is sampled by current probe 204 coupled to input 206 of gain-phase meter 208. The voltage across wettability cell 100 from the AC signal output by generator 202 is provided to input 210 of gain-phase meter 208. Gain-phase meter 208 may be embodied in a commercial phase meter unit such as a Hewlett Packard HP 3575A gain-phase meter. Gain-phase meter 208 outputs, on output 212, signals corresponding to the ratio of the magnitude of the voltage across wettability cell 100, to the magnitude of the current into wettability cell 100, and the phase angle of the current relative to the voltage. The ratio of the magnitude of the voltage to the magnitude of the current is the magnitude of the complex impedance. Output 212 is coupled to data processor 214. The signals representing the magnitude of the impedance signal and the phase output by gain-phase meter 208 are processed by data processor 214 to output the complex impedance of wettability cell 100. Data processor 214 also generates the equivalent parallel capacitance and the resistance corresponding to the complex impedance of cell 100.

When there is an oil film present on the surface of electrodes 116 and 118, the electrical impedance of wettability cell 100 appears as a resistor in parallel with a capacitor. The resistance, R, and capacitance, C, values may be determined by data processor 214 from the voltage, current, and phase signals in accordance with Equations (1)–(3):

$$|Z|=|V|/|I| \qquad (1)$$

$$R=|Z|\cos\phi \qquad (2)$$

$$C=\tan \phi/(2\pi fR) \qquad (3)$$

Here $|V|$ is the voltage magnitude signal, $|I|$ the current magnitude signal, $|Z|$ is the magnitude of the complex impedance, and $\phi$ the phase signal at output 212, and f is a preselected frequency of oscillator 202.

Figure 3:
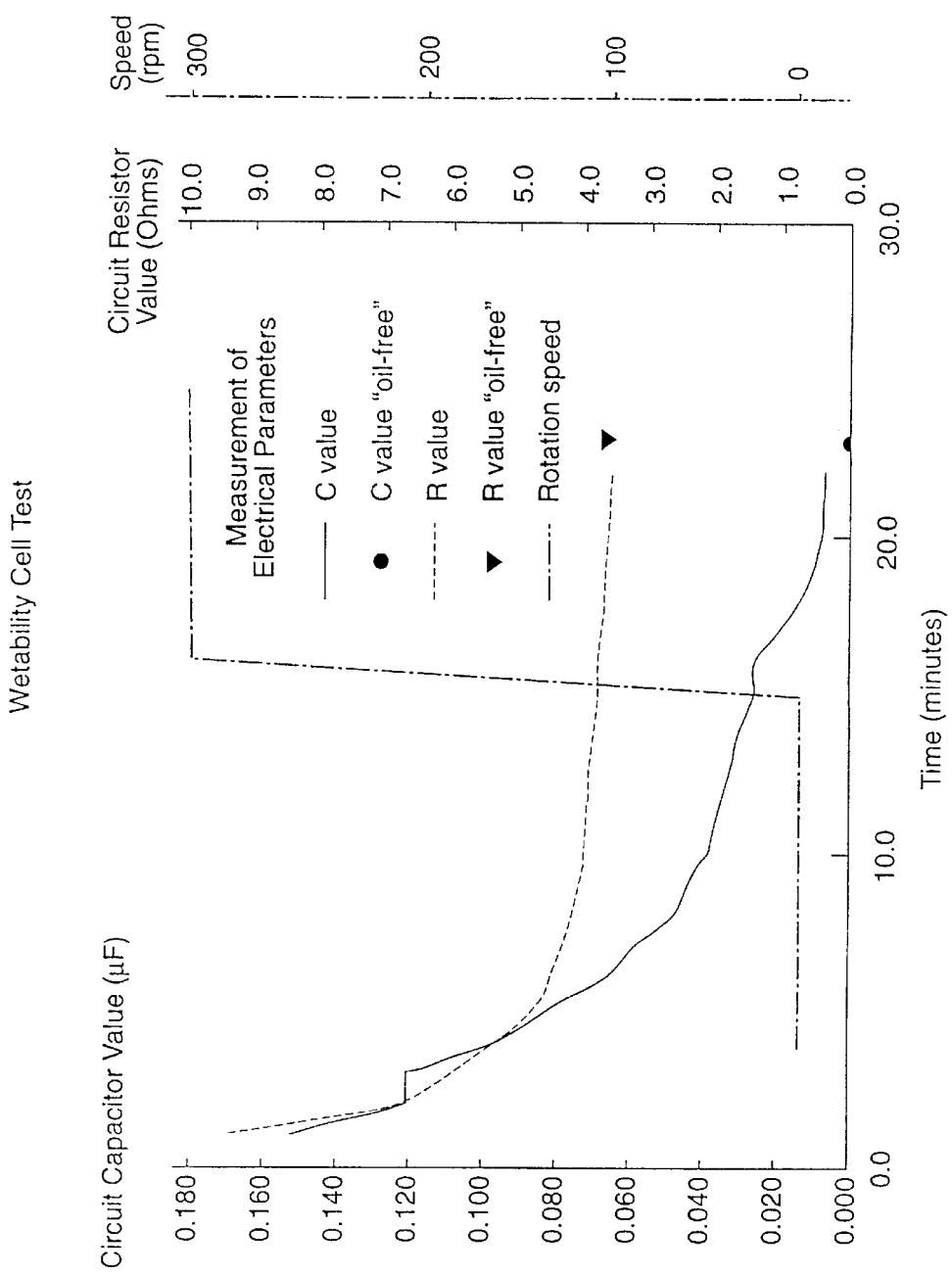
FIG. 3 illustrates, in graphical form, a complex impedance of a wettability cell in accordance with an embodiment of the present invention.

The present invention may be further understood by referring now to FIG. 3 illustrating, in graphical form, the results of a wettability measurement according to the present invention. The resistance (dashed curve) and the capacitance (solid curve) appearing between electrodes 116 and 118 are shown as a function of the immersion time of cell 100 in a surfactant solution. The resistance asymptotes to a value of approximately 3.5 ohms while the capacitance values drop continuously until reaching a plateau at approximately 15 minutes. The continuing decrease of the capacitance signals the removal of the oil film by the surfactant solution. However, in the absence of agitation, the surfactant solution alone leaves a portion of the oil film remaining on electrodes 116 and 118. At approximately 16 minutes, rotating sleeve portions 108 and 109 are set into rotation (dash-dot curve) to a speed of 300 revolutions-per-minute (RPM). The shear forces generated thereby effect further removal of the oil film by the surfactant solution until approximately 22 minutes at which time the rotation of sleeve portions 108 and 109, and the experiment, illustrated in FIG. 3, terminate. The thickness of the remaining oil film is approximately four thousandths of an inch (0.004"). The "oil-free" values of resistance (solid triangle) and capacitance (solid circle) are obtained after mechanical cleaning of the electrodes with surfactant and a brush. These show that the capacitive portion of the complex impedance is essentially zero when the electrodes are oil-free. Although agitation of the surfactant did not remove all of the oil film in the experiment of FIG. 3, it would be understood that further agitation of the surfactant solution by rotation of sleeve portions 108 and 109 may remove additional amounts of the oil film.

Thus, the present invention may be used to test the efficacy of the removal of oil films due to oil-based drilling muds. Application times for a particular surfactant solution may be inferred by observing oil-film thickness, as represented by the capacitive portion of the complex impedance between the cell electrodes, as a function of time. Oil-film removal as a function of solution agitation, is represented by rotation of rotating sleeve portions 108 and 109. The rotation may be correlated with the pumping speed of the surfactant in the well bore and the resulting vertical flow between the drill pipe and the casing or formation. Additionally, different surfactant solution formulations may be tested to determine their effectiveness in removing the oil film.

Although the present invention and its advantages have been described in detail, it should be understood that various changes, substitutions and alterations can be made herein without departing from the spirit and scope of the invention as defined by the appended claims.

What is claimed is:

1. An apparatus for wettability measurement comprising:
   an annular member having an inner surface, said annular member being adaptable for immersion in a fluid;
   first and second electrodes affixed to said inner surface of said annular member, wherein said electrodes each have a surface operable for supporting an oil film; and
   an insulator affixed to said inner surface and disposed between said first and second electrodes, said first and second electrodes being coupled with circuitry for measuring a complex impedance therebetween, said complex impedance having phase related portions providing a measure of wettability affecting material.

2. The apparatus of claim 1 further comprising:
   a rotatable member disposed in an interior of said annular member, said rotatable member being rotatable relative to said annular member for generating shear forces in said fluid, said shear forces for modifying a wettability effect of said oil film.

3. The apparatus of claim 1 wherein said fluid comprises a surfactant solution.

4. The apparatus of claim 1 further comprising an alternating current (AC) signal generator coupled between said first and second electrodes for generating an alternating current signal therebetween, a ratio between a voltage and a current of said AC signal to said current flow thereby defining said complex impedance.

5. The apparatus of claim 1 wherein a composition of said first and second electrodes comprises steel.

6. The apparatus of claim 1 further comprising phase metering circuitry coupled to said first and second electrodes for measuring said complex impedance.

7. The apparatus of claim 4 wherein a frequency of said AC signal is in an interval from ten kilohertz (10 kHz) to one megahertz (1 MHZ).

8. The apparatus of claim 1 wherein a thickness of said oil film is correlated with a capacitive portion of said complex impedance.

9. A method of wettability affecting measurement comprising the steps of:
   immersing a pair of electrodes operable for supporting an oil film in a conducting solution;
   determining a complex impedance between said electrodes; and
   evaluating a phase differentiated portion of said complex impedance to determine a wettability affect of said oil film.

10. The method of claim 9 wherein said step of determining said complex impedance further comprises the steps of:
    applying an alternating current (AC) signal to the pair of electrodes;
    measuring an AC voltage of said AC signal and an AC current flowing into said electrodes; and
    determining a phase of said AC current to said AC voltage.

11. The method of claim 9 wherein said conducting solution comprises a surfactant solution.

12. The method of claim 9 further comprises the step of agitating said conducting solution.

13. The method of claim 12 wherein said agitating step comprises the step of rotating a stirring member proximal to said first and second electrodes.

14. The method of claim 13 wherein said stirring member comprises a substantially cylindrical surface.

15. The method of claim 9 wherein a thickness of said oil film is correlated with a capacitive portion of said complex impedance.

16. The method of claim 12 further comprising the step of measuring a capacitive portion of said complex impedance for a period of time to determine a thickness of said oil film as a function of said agitation.

17. An apparatus for wettability measurement comprising:
    a wettability cell, said wettability cell comprising:
       a stationary housing containing a drive means for rotating a driven member;
       a rotating sleeve including an upper portion having a shaft coupled to said drive means for rotation thereby, and a lower portion for agitating a surfactant solution;
       a stationary cylinder disposed about said rotating sleeve, said stationary cylinder having a lower portion, including an inner shell and an outer shell with a gap therebetween;
       first and second electrodes affixed against an incised inner surface of said inner shell;
       an insulator affixed against said incised inner surface of said inner shell, said insulator disposed between said first and second electrodes; and
       a pair of wires, each connected to one of said first and second electrodes, said pair of wires passing through said gap;
    a transformer having a primary coupled to said pair of wires;

an oscillator coupled to a secondary of said transformer for supplying an alternating current (AC) signal thereto;

a phase/voltage meter having a first input for measuring a voltage of said AC signal;

a current probe for measuring a current of said AC signal coupled to a second input of said phase/voltage meter, wherein said phase/voltage meter outputs output signals corresponding to a magnitude of said voltage, a magnitude of said current and a phase of said current relative to said voltage; and a data processor coupled to said phase/voltage meter for receiving said output signals, said data processor generating signals corresponding to a resistive portion and a capacitive portion of a complex impedance between said electrodes in response thereto, said capacitive portion providing an indication of said wettability.

18. A method for evaluating the effect of a conducting solution on a characteristic of a test material, comprising the steps of:

combining a test material with two electrically distinct electrodes;

immersing said electrodes and combined test material into an electrically conductive solution;

applying an alternating current between said electrodes;

determining a first phase related complex impedance between said electrodes at a first point in time; and correlating one or more components of said complex impedance with a characteristic of said test material.

19. The method as defined in claim 18, comprising the further steps of:

determining a second phase related complex impedance between said electrodes at a second, later point in time;

comparing said first and second complex impedances to determine a change in said complex impedances; and evaluating the effect of said conductive solution in changing said test material as a function of said change in said complex impedance.

20. The method as defined in claim 19, comprising the further step of generating a shear flow of said electrically conductive solution between said electrodes between said first and second points in time.

21. The method as defined in claim 18 wherein an electrical capacitive portion of said complex impedance is employed to determine a measure of said test material.

22. The method as defined in claim 21 wherein said electrical capacitive portion of said complex impedance is employed to determine a thickness of said test material.

23. The method as defined in claim 18 wherein said test material comprises a film of oil and said complex impedance is employed to determine the thickness of said film of oil.

24. The method as defined in claim 22 wherein said test material comprises a film of oil and said complex impedance is employed to determine the thickness of said film of oil.

25. The method as defined in claim 20 wherein an electrical capacitive portion of said complex impedance is employed to determine a measure of said test material.

26. A method as defined in claim 25 wherein said electrical capacitive portion of said complex impedance is employed to determine a thickness of said test material.

27. The method as defined in claim 26 wherein said test material comprises a film of oil and said complex impedance is employed to determine the thickness of said film of oil.

28. The method as defined in claim 27 wherein said conductive solution comprises a surfactant solution.

29. The method as defined in claim 28 wherein said surfactant solution includes a salt.

30. The method as defined in claim 20 wherein said shear flow is generated by a mechanical movement through said conductive solution.

31. The method as defined in claim 30 wherein said mechanical movement is imparted by an electric motor.

32. The method as defined in claim 31 wherein said electrodes are stationary relative to said mechanical movement.

33. The method as defined in claim 18 wherein said alternating current may range in frequency from 10 KHz to 1 MHz.

34. The method as defined in claim 18 wherein capacitive and resistive components of said complex impedance are determined.

* * * * *